United States Patent
Kitaoka et al.

[11] 3,995,053
[45] Nov. 30, 1976

[54] ACARICIDAL AND INSECTICIDAL COMPOSITIONS

[75] Inventors: Shigeo Kitaoka, Musashino; Katsuhiro Johkoh, Yokohama; Hisashi Ebisawa; Tadashi Sato, both of Tokyo; Hiroshi Kubo; Sosuke Takahashi, both of Yokohama; Yoshinobu Kawase, Tokyo, all of Japan

[73] Assignee: Showa Denko Kabushiki Kaisha, Tokyo, Japan

[22] Filed: Oct. 18, 1974

[21] Appl. No.: 515,929

[30] Foreign Application Priority Data
Oct. 23, 1973 Japan............................ 48-118458

[52] U.S. Cl. ................................................ 424/304
[51] Int. Cl.² ...................... A01N 9/06; A01N 9/20
[58] Field of Search ............................ 424/304, 330

[56] References Cited
UNITED STATES PATENTS
3,175,896  3/1965  Arndt et al. .................... 424/330
3,852,437  12/1974  Helfenberger .................. 424/304
3,855,292  12/1974  Wollweber et al. ............. 424/304

*Primary Examiner*—Albert T. Meyers
*Assistant Examiner*—D. W. Robinson
*Attorney, Agent, or Firm*—Sherman & Shalloway

[57] ABSTRACT

An acaricidal and insecticidal composition containing as an active ingredient a carbodiimide of the formula

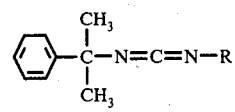

wherein R is a member selected from the class consisting of acyclic and cyclic alkyl groups containing 2–18 carbon atoms, a phenyl group, and a phenyl group substituted by at least one substituent of the group consisting of alkyl groups of 1–4 carbon atoms, alkoxy groups of 1–4 carbon atoms and chlorine.

11 Claims, No Drawings

ACARICIDAL AND INSECTICIDAL COMPOSITIONS

This invention relates to an acaricidal and insecticidal composition containing as its active ingredient a carbodiimide having the formula

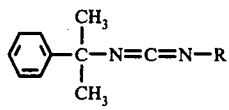  (I).

wherein R is either a chain or cyclic alkyl group containing 2–18 carbon atoms, a phenyl group, or a phenyl group substituted by at least one substituent from the class consisting of an alkyl group of 1–4 carbon atoms, an alkoxy group of 1–4 carbon atoms and chlorine.

The carbodiimides of formula I defined above are referred to herein as the compounds of the invention.

It has now been found that the compounds of the invention have superior pesticidal power against a wide variety of hygienic and agricultural pests and especially that their exterminatory action against mites and harmful insects, and particularly mites and ticks is outstanding.

Of the mites the Tetranychidae are considered to cause the most serious damage to fruits, vegetables and flowering plants. Heretofore, the organic chlorine type compounds, sulfone type compounds and numerous other chemicals have been suggested and have been used as agricultural and horticultural pesticides for exterminating these mites. However, few have had a satisfactory direct acaricidal power. Now, as typical mites that live on livestocks, known are such ticks as *Boophilus microplus* and *Haemaphysalis longicornis*. Since these mites that live on livestocks cause exceedingly great damages, there has been strong demand for a long time for a powerful chemical that can exterminate these mites or prevent their development.

The object of the present invention is to provide a new acaricidal and insecticidal composition having a strong activity as well as a method of exterminating mites and insects.

The compounds of the invention are effective against all stages of development, i.e., the egg, larval and adult stages, of mites and insects. Their effects of destroying the eggs of mites are especially marked. A surprising fact is that the compounds of the invention are even effective in destroying the ovipositing ability of mites. The *Boophilus microplus*, which lives on livestock and also serves as a vector or pathogenic piroplasma, lays its eggs in pastures where the eggs develop into adult and then infest, for example, cattle. This tick has a considerably large body. The female has a body length of about 8 millimeters, while the male is about 3 millimeters long. The ability of this tick to survive is great. While the compounds of the invention can usually destroy the eggs of ticks with a given concentration, for example, a concentration of about 15 ppm, the oviposition itself can be inhibited by the application of the compounds of the invention to the surface of the body of animals infested with ticks or to pastures at such a low concentration that the eggs are not destroyed. Hence, it is possible to prevent the infestation by means of ticks at the source and thus effect the extermination of ticks. This is one of the great features of the compounds of the invention.

The toxicity of the compounds of the invention to mammals is extremely small, and it causes practically no harm to plants. In a test conducted by oral administration of the compounds of the invention to mouse, the $LD_{50}$ was in all instances more than 4000 mg/Kg, some compounds exhibiting even as high as about 15,000 mg/Kg.

The compounds of the invention, which are usually nonvolatile liquids, can be applied as such, or after dilution with diluents or fillers, to the place of origin of the mites or the place of their infestation. In using the compounds of the invention in a diluted state, they can be used in the following manner. For instance, they can be used as a wettable powder by mixing and comminuting them along with an emulsifier and a solid filler, following which the so obtained powder is suspended in water at the time of their use. They can be used as an emulsion by dissolving them in an organic solvent along with an emulsifier followed by dilution with water at the time of their use. Further, they can be used in the form of an oral preparation by merely dissolving them in an organic solvent. Still further, they can be impregnated in solid fillers and used as dusting powders, granules, and tablets. As examples of the usable carrier materials, fillers and organic solvents, included are such materials as clay, talc, bentonite, diatomaceous earth, starch, kaolin, benzene, xylene, kerosene, ketones, dimethylformamide, Freon, etc. Thus, the acaricidal and insecticidal compositions of the present invention are the compounds of formula (I) as such or intimate mixture of said compounds with solid or liquid diluents or fillers. In the case of the wettable powder and emulsion, the compounds of the invention are applied diluted to usually about 1/100 to about 1/3000 of their original strength. On the other hand, in the case of the dusting powders, granules and tablets, these are applied in a state wherein the compounds of the invention are contained therein in a concentration of about 0.5 to about 10%. The application can be made by such procedures as spraying, dusting, scattering and the like. The application can be made to any place where mites and insects develop, grow and inhabit, for example, to the surface of the leaves of plants inside a greenhouse and, in the case of outdoors, to fields where crops are growing and to pastures. While some of the compounds of the invention are new, they can all be prepared in a simple manner by conventional processes. For example, these compounds can be obtained by dehydrosulfurnizing the thiourea derivative of the formula

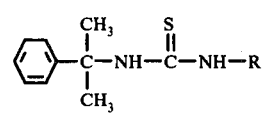

with either NaOCl, HgO, PbO or PbCO$_3$, or by submitting the urea derivative of the formula

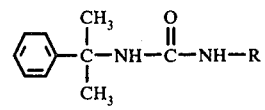

to a dehydration reaction using p-toluene sulphonyl chloride in pyridine or by using $P_2O_5$.

Two specific examples illustrating the synthesis of the present invention will be given below.

Synthesis of N-n-octyl-N'-(2-phenyl-2-propyl)carbodiimide

A mixture of 14.2 grams of N-n-octyl-N'-2-phenyl-2-propyl)-thiourea, 20 grams of basic lead carbonate and 100 ml of dry xylene was heated under reflux for 3 hours. The reaction liquid was then separated by filtration followed by concentration of the mother liquor, whereupon N-n-octyl-N'-(2-phenyl-2-propyl)carbodiimide of high purity was obtained. When this was distilled further, 10.1 grams of the intended product of b. p. 121° – 3° C./0.15 mm Hg was obtained as a pure product.

Synthesis of N-p-methoxy-o-tolyl-N'-(2-phenyl-2-propyl)carbodiimide

A mixture of 6.0 grams of N-(p-methoxy-o-tolyl)-N'-(2-phenyl-2-propyl)-urea, 5.7 grams of p-toluene sulfonyl chloride and 30 ml of pyridine was reacted for 2 hours at 60° C. The reaction mixture was then cooled with ice to separate out the pyridine salt, after which the precipitated salt was filtered off, and the mother liquor was concentrated. Xylene was added, and the residual salt was filtered off. When the mother liquor was then concentrated, the intended product was obtaind in high purity. The yield was 4.1 grams.

Specific examples of desirable compounds of the invention include the following compounds. For convenience of reference, the compounds have been numbered. Of those compounds, most preferred are the compounds Nos. 7–12.

| Compound No. | |
|---|---|
| 1 | N-ethyl-N'-(2-phenyl-2-propyl)carbodiimide |
| 2 | N-n-propyl-N'-(2-phenyl-2-propyl)-carbodiimide |
| 3 | N-iso-propyl-N'-(2-phenyl-2-propyl)carbodiimide |
| 4 | N-sec-butyl-N'-(2-phenyl-2-propyl)-carbodiimide |
| 5 | N-tert-butyl-N'-(2-phenyl-2-propyl)-carbodiimide |
| 6 | N-n-pentyl-N'-(2-phenyl-2-propyl)-carbodiimide |
| 7 | N-n-hexyl-N'-(2-phenyl-2-propyl)-carbodiimide |
| 8 | N-n-heptyl-N'-(2-phenyl-2-propyl)-carbodiimide |
| 9 | N-n-octyl-N'-(2-phenyl-2-propyl)-carbodiimide |
| 10 | N-n-nonyl-N'-(2-phenyl-2-propyl)-carbodiimide |
| 11 | N-n-decyl-N'-(2-phenyl-2-propyl)-carbodiimide |
| 12 | N-n-dodecyl-N'-(2-phenyl-2-propyl)-carbodiimide |
| 13 | N-n-myristyl-N'-(2-phenyl-2-propyl)-carbodiimide |
| 14 | N-n-cetyl-N'-(2-phenyl-2-propyl)-carbodiimide |
| 15 | N-n-stearyl-N'-(2-phenyl-2-propyl)-carbodiimide |
| 16 | N-(2-ethyl-n-hexyl)-N'-(2-phenyl-2-propyl)carbodiimide |
| 17 | N-phenyl-N'-(2-phenyl-2-propyl)-carbodiimide |
| 18 | N-p-tolyl-N'-(2-phenyl-2-propyl)-carbodiimide |
| 19 | N-p-propylphenyl-N'-(2-phenyl-2-propyl)-carbodiimide |
| 20 | N-2,4-xylyl-N'-(2-phenyl-2-propyl)-carbodiimide |
| 21 | N-p-methoxyphenyl-N'-(2-phenyl-2-propyl)carbodiimide |
| 22 | N-p-propoxyphenyl-N'-(2-phenyl-2-propyl)carbodiimide |
| 23 | N-p-methoxy-o-tolyl-N'-(2-phenyl-2-propyl)carbodiimide |
| 24 | N-3,4-dichlorophenyl-N'-(2-phenyl-2-propyl)carbodiimide |
| 25 | N-(3-chloro-4-methoxyphenyl)-N'-(2-phenyl-2-propyl)carbodiimide |
| 26 | N-cyclohexyl-N'-(2-phenyl-2-propyl)-carbodiimide |

Recipes of the acaricidal and insecticidal compositions of the invention are shown below. In the recipes the parts are on a weight basis.

| Recipe 1 (emulsion) | Parts |
|---|---|
| Compound No. 10 | 50 |
| Xylene | 15 |
| Nonionic emulsifier (SORPOL, a product of Toho Chemical Co., Japan | 35 |

The foregoing ingredients are mixed and rendered into an emulsion. In using this emulsion, it is diluted with water and applied.

| Recipe 2 (wettable powder) | Parts |
|---|---|
| Compound No. 7 | 20 |
| Diatomaceous earth-clay mixture | 75 |
| Polyoxyethylenealkylphenol ether type emulsifier | 5 |

The foregoing ingredients are rendered into a wettable powder by mixing and comminuting the ingredients. In using this wettable powder, it is suspended in water and applied.

| Recipe 3 (dusting powder) | Parts |
|---|---|
| Compound No. 8 | 2 |
| Talc-clay mixture | 98 |

The foregoing ingredients are rendered into a dusting powder by mixing and comminuting the ingredients. This is directly applied.

Next, there will be shown the tests that were conducted to determine the effectiveness of the acaricidal and insecticidal compositions of the invention.

TEST 1

A test for determining the insecticidal effectiveness against housefly (*Musca domestica Vicina*) and azuki-bean weevil (*Callosobruchus clinensis Linnaeus*)

Two milliliters of each of the solutions of the several test compounds enumerated in Table 1 diluted to a concentration of 1000 ppm was placed in a Petri dish of 9-cm diameter, and the acetone was evaporated therefrom at room temperature. Twenty-five housefly imagoes 3–5 days after their emergence were then placed in each of the dishes and were fed a sugar solution impregnated in filter paper. After the passage of 24 hours, mortality was checked. A similar test was carried out on azuki-bean weevils two days after their emergence, and the insecticidal effectiveness of the several compounds were determined after 24 hours.

The results of these tests are shown in Table 1.

Table 1

| Compound No. | Insecticidal Rate (%) after 24 hours | |
|---|---|---|
| | Housefly | Azuki-bean weevil |
| 1 | 100 | 80 |
| 2 | 100 | 100 |
| 3 | 100 | 100 |
| 4 | 100 | 100 |
| 5 | 100 | 100 |
| 6 | 100 | 100 |
| 7 | 100 | 100 |
| 8 | 100 | 100 |
| 9 | 100 | 100 |
| 10 | 100 | 100 |
| 11 | 100 | 100 |
| 12 | 100 | 100 |
| 13 | 85 | 90 |
| 14 | 80 | 75 |
| 17 | 100 | 100 |
| 18 | 100 | 100 |
| 19 | 90 | 95 |
| 20 | 100 | 100 |
| 21 | 100 | 100 |
| 22 | 100 | 90 |
| 23 | 100 | 100 |
| 24 | 100 | 100 |
| 25 | 100 | 100 |
| 26 | 100 | 100 |
| Control (untreated) | 0 | 0 |

TEST 2

Test of effectiveness in killing imagoes of Kanzawa spider mite (*Tetranychus kanzawai* Kishida)

A primordial leaf of a bean plant was inoculated with 20 Kanzawa spider mites. One day after the inoculation, the leaf was dipped for 2–3 seconds in chemical liquids of the test compounds prepared into wettable powders in accordance with the aforementioned Recipe 2 and of a concentration of 62.5 ppm. Twenty-four hours after this treatment with the chemicals, the rate of imagoes killed was examined. The results of the test are shown in Table 2.

Table 2

| Compound No. | Rate of Imagoes Killed (%) |
|---|---|
| 6 | 87 |
| 7 | 100 |
| 8 | 100 |
| 9 | 100 |
| 10 | 100 |
| 11 | 100 |
| 12 | 100 |
| 24 | 100 |
| Control (untreated) | 5 |

In the case of compounds Nos. 7–12, it was found that these compounds had fully satisfactory effectiveness in killing imagoes even when the concentration was diluted to one-tenth of that indicated above.

TEST 3

Test of effectiveness in killing eggs of Kanzawa spider mite

A primordial leaf of a bean plant was cut into a disc shape having a diameter of 33 millimeters and was secured to agar contained in a Petri dish. The surface of the leaf disc was then inoculated with 15 Kanzawa spider mites.

Twenty-four hours later, the imagoes were removed, and the number of eggs laid was examined, after which the laid eggs were left to stand for 24 hours. The leaf disc on which the eggs were laid was then dipped for 30 seconds in chemical liquids of the test compounds prepared into wettable powders in accordance with the aforementioned Recipe 2 and diluted to a concentration of 62.5 ppm. Three days after the chemical treatment, the ovicidal rate was examined. By way of comparison, the same test was carried out using Control Chemical I. Control Chemical I has tricyclohexyltin hydroxide as its active ingredient and is known as being a powerful acaricidal preparation. The results obtained are shown in Table 3.

Further, the same test was carried out with the foregoing compounds reducing the concentration to one-fourth of that used above. The compounds of the invention were in all cases more powerful in their effectiveness than that of Control Chemical I, the compounds Nos. 6, 7, 8, 9, 10, 11, 12, 19, 20 and 24 being most effective. The results obtained are shown in Table 4.

Table 3

| Compound No. | Rate of Kanzawa Spider Mite Eggs Killed (%) | Compound No. | Rate of Kanzawa Spider Mite Eggs Killed (%) |
|---|---|---|---|
| 6 | 100 | 17 | 100 |
| 7 | 100 | 18 | 100 |
| 8 | 100 | 19 | 100 |
| 9 | 100 | 20 | 95 |
| 10 | 100 | 21 | 94 |
| 11 | 100 | 22 | 99 |
| 12 | 100 | 24 | 100 |
| 13 | 100 | Control chemical I | 96 |
| 14 | 89 | | |

Table 4

| Compound No. | Rate of Kanzawa Spider Mite Eggs Killed (%) | Compound No. | Rate of Kanzawa Spider Mite Eggs Killed (%) |
|---|---|---|---|
| 6 | 100 | 14 | 68 |
| 7 | 100 | 17 | 66 |
| 8 | 100 | 18 | 72 |
| 9 | 100 | 19 | 100 |
| 10 | 100 | 20 | 93 |
| 11 | 100 | 21 | 75 |
| 12 | 100 | 22 | 73 |
| 13 | 60 | 24 | 90.3 |
| | | Control chemical I | 35.0 |

In the case of the compounds Nos. 7–12, it was found that their ovicidal effectiveness was fully satisfactory even when the concentration was diluted to about 8 ppm.

TEST 4

Test of effectiveness in killing the imagoes and eggs of citrus red mites (*Pononychus citri* McGregor)

The experiment for testing the effectiveness of killing imagoes and eggs of citrus red mite was conducted by the agar method as described in Test 3. The imagoes of citrus red mite used in the test were those collected from mandarin oranges infested with these mites. The results of the imago killing test are shown in Table 5.

Table 5

| Compound No. | Rate of Killed Imagoes of Citrus red mite (%) | |
|---|---|---|
| | After 24 hours | After 48 hours |
| 6 | 70.6 | 84.3 |
| 7 | 82.4 | 100 |
| 8 | 95.1 | 100 |
| 9 | 90.3 | 100 |
| 10 | 92.5 | 100 |
| 11 | 98.1 | 100 |
| 12 | 91.6 | 100 |
| 24 | 94.6 | 100 |
| Control (untreated) | 5.2 | 10.5 |

Note:
Concentration of chemical: 62.5 ppm
After the treatment the imagoes were cared for in a breeding chamber held at 25° ± 1° C.

The results of the ovicidal test are shown in Table 6.

Table 6

| Compound No. | Rate of Citrus red mite eggs killed (%) | | Compound No. | Rate of Citrus red mite eggs killed (%) | |
|---|---|---|---|---|---|
| | After 6 days | After 7 days | | After 6 days | After 7 days |
| 6 | 95.3 | 100 | 17 | 79.8 | 88.6 |
| 7 | 100 | 100 | 18 | 86.4 | 90.2 |
| 8 | 100 | 100 | 19 | 100 | 100 |
| 9 | 100 | 100 | 20 | 91.3 | 96.0 |
| 10 | 100 | 100 | 21 | 82.7 | 90.3 |
| 11 | 100 | 100 | 22 | 84.4 | 94.2 |
| 12 | 100 | 100 | 24 | 94.8 | 99.5 |
| 13 | 60.5 | 79.6 | Control chemical II | 81.0 | 89.5 |
| 14 | 83.6 | 92.8 | Control (untreated) | 10.6 | 15.0 |

Note:
Concentration of chemical: 62.5 ppm.
After the treatment, the eggs were cared for in a breeding chamber held at 25° ± 1° C.

Control Chemical II is a commercial acaricidal preparation for citrus red mites. It contains as active ingredient a mixture of

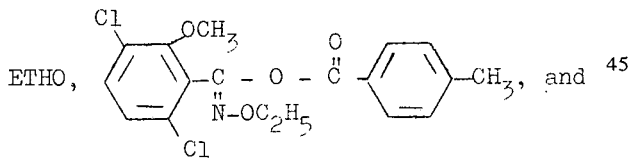

and

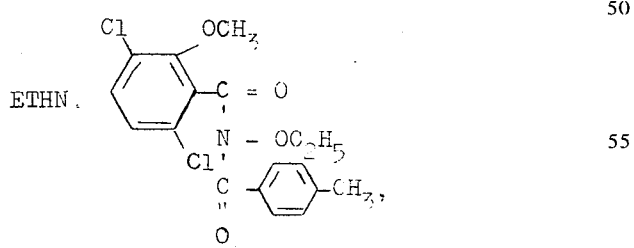

in a ratio of ETHO : ETHN of 6 : 1.

TEST 5

Test of the effectiveness in inhibiting the oviposition by *Boophilus microplus*

One each of the imagoes of female *Boophilus microplus* which had been allowed to suck blood fully was placed in a flat bottom test tube having a diameter of 10 millimeters and a depth of 35 millimeters. After rendering the chemicals to be tested into acetone solutions, the solutions were dropped to the back of the mites in an amount corresponding to 110 gamma per one gram of body weight, using a micro syringe, after which the acetone was evaporated. The test tube was then transferred to a desiccator containing a small portion of water where it was left standing at a constant temperature of 30° C., and the ticks were allowed to oviposit. Two weeks later, the amount of eggs laid per 1 gram of body weight was counted. Using this value and the amount of eggs laid in the case of the control group not treated with the chemicals, the rate of inhibition of oviposition was obtained as follows:

$$\text{Rate of inhibition of oviposition} = \frac{A - B}{A} \times 100$$

where

A is the number of eggs laid per gram of body weight of ticks of the group not treated with chemicals.

B is the number of eggs laid per gram of body weight of ticks of the group treated with chemicals.

The foregoing rate was used to indicate the effectiveness of the chemicals tested.

By way of comparison, the same test was conducted with Control Chemicals III and IV. Control Chemicals III and IV are known as being powerful acaricidal preparations, their active ingredients being N'-(2-methyl-4-chlorophenyl)-N,N-dimethyl formamidine and 1-naphthyl-N-methylcarbamate, respectively.

The results of the tests are shown in Table 7.

Table 7

| Compound No. | Rate of Inhibition of Oviposition by Boophilus microplus (%) |
|---|---|
| 2 | 100 |
| 7 | 96.3 |
| 8 | 100 |
| 9 | 100 |
| 10 | 100 |
| 11 | 93.1 |
| 12 | 100 |
| Control Chemical III (100 γ/g) | 76.6 |
| (110 γ/g) | 78.2 |
| Control Chemical IV (100 γ/g) | 26.7 |
| (110 γ/g) | 27.0 |
| Control (untreated) | 0 |

In the case of compounds Nos. 7–12, it was found that these compounds had fully satisfactory effectiveness in inhibiting oviposition even when the concentration was diluted to one-tenth of that indicated above.

TEST 6

Test of effectiveness in inhibiting the oviposition by *Boophilus microphus* as well as effectiveness in killing the imagoes thereof.

An emulsion was prepared in accordance with the foregoing Recipe 1, using as its active ingredient compound No. 12. Several classes of spraying liquids having the concentrations indicated in Table 6 were prepared by diluting this emulsion with water. Ten female *Boophilus microplus* which had sucked blood fully were placed on a filter paper, and the liquid described above was sprayed onto the ticks with a glass sprayer in an amount such that the liquid would flow down the backs of the ticks. The ticks were then immediately transferred to a wet filter paper disposed in a Petri dish, and when the liquid on the backs of the ticks became somewhat dried, the dish was covered. The Petri dish was then held at a constant temperature of 30° C. for two weeks, after which the total amount of eggs laid was counted. During the time the Petri dish was held at a constant temperature, the inside of the Petri dish was maintained in a state of high humidity by dropping a small amount of water onto the filter paper daily. The effectiveness was judged by the rate of eggs laid by the several treated groups relative to the total eggs laid in the case of the ticks of the control group, which had been sprayed only with water. On the other hand, the effectiveness in killing the female imagoes was judged by observation of the presence or absence of deaths. The case where the presence of deaths was observed is indicated with the symbol (+), and the case where there were no deaths is indicated with the symbol (−).

The results obtained are shown in Table 8.

Table 8

| Concentration of Compound (%) | Rate of Eggs Laid (%) | Effectiveness in Killing Imagoes |
|---|---|---|
| 1 | 0 | (+) |
| 0.3 | 0 | (+) |
| 0.1 | 0 | (+) |
| 0.03 | 62.6 | (−) |
| 0.01 | 85.5 | (−) |
| 0.003 | 94.8 | (−) |

What is claimed is:

1. An acaricidal and insecticidal composition containing as an active ingredient a carbodiimide of the formula

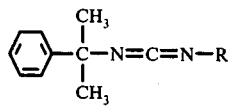

wherein R is a member selected from the class consisting of: (1) acyclic alkyl groups containing 2–18 carbon atoms; (2) cyclic alkyl groups containing 3–18 carbon atoms; (3) a phenyl group; and (4) a phenyl group substituted by at least one substituent of the group consisting of alkyl groups of 1–4 carbon atoms, alkoxy groups of 1–4 carbon atoms and chlorine; said active ingredient being present in an acaricidally and insecticidally effective amount of not less than 8 ppm, the other components in the composition being diluents or fillers.

2. The acaricidal and insecticidal composition of claim 1 wherein said active ingredient is N-n-octyl-N'-(2-phenyl-2-propyl)carbodiimide.

3. The acaricidal and insecticidal composition of claim 1 wherein said active ingredient is N-n-dodecyl-N'-(2-phenyl-2-propyl)carbodiimide.

4. The acaricidal and insecticidal composition of claim 1 wherein said active ingredient is N-n-heptyl-N'-(2-phenyl-2-propyl)carbodiimide.

5. The acaricidal and insecticidal composition of claim 1 wherein said active ingredient is N-n-nonyl-N'-(2-phenyl-2-propyl)carbodiimide.

6. The acaricidal and insecticidal composition of claim 1 wherein said active ingredient is N-n-hexyl-N'-(2-phenyl-2-propyl)carbodiimide.

7. The acaricidal and insecticidal composition of claim 1 wherein said active ingredient is N-n-decyl-N'-(2-phenyl-2-propyl)carbodiimide.

8. The acaricidal and insecticidal composition of claim 1 wherein said active ingredient is N-n-pentyl-N'-(2-phenyl-2-propyl)carbodiimide.

9. The acaricidal and insecticidal composition of claim 1 wherein said active ingredient is N-p-propylphenyl-N'-(2-phenyl-2-propyl)carbodiimide.

10. The acaricidal and insecticidal composition of claim 1 wherein said active ingredient is N-2,4-xylyl-N'-(2-phenyl-2-propyl)carbodiimide.

11. The acaricidal and insecticidal composition of claim 1 wherein said active ingredient is N-3,4-dichlorophenyl-N'-(2,phenyl-2-propyl)carbodiimide.

* * * * *